US012564698B1

(12) United States Patent
Sanders

(10) Patent No.: US 12,564,698 B1
(45) Date of Patent: Mar. 3, 2026

(54) PATIENT INSUFFLATION SYSTEMS AND METHODS

(71) Applicant: Hollie Sanders, Bessemer, AL (US)

(72) Inventor: Hollie Sanders, Bessemer, AL (US)

( * ) Notice: Subject to any disclaimer, the term of this patent is extended or adjusted under 35 U.S.C. 154(b) by 698 days.

(21) Appl. No.: 18/070,131

(22) Filed: Nov. 28, 2022

(51) Int. Cl.
| | |
|---|---|
| *A61M 16/20* | (2006.01) |
| *A61M 13/00* | (2006.01) |
| *A61M 16/08* | (2006.01) |
| *A61M 16/10* | (2006.01) |

(52) U.S. Cl.
CPC ........ *A61M 16/209* (2014.02); *A61M 13/003* (2013.01); *A61M 16/0816* (2013.01); *A61M 16/0833* (2014.02); *A61M 16/1005* (2014.02); *A61M 16/104* (2013.01); *A61M 16/208* (2013.01); *A61M 2202/0208* (2013.01)

(58) Field of Classification Search
CPC ............ A61M 13/003; A61M 16/0833; A61M 16/209; A61M 16/0875; A61M 2202/0208
See application file for complete search history.

(56) References Cited

U.S. PATENT DOCUMENTS

| | | | | | |
|---|---|---|---|---|---|
| 5,101,820 | A | * | 4/1992 | Christopher | .......... A61M 16/10 |
| | | | | | 128/207.14 |
| 5,582,165 | A | * | 12/1996 | Bryan | ................ A61M 25/0111 |
| | | | | | 128/207.14 |
| 7,320,324 | B2 | * | 1/2008 | Willeford | .......... A61M 16/0463 |
| | | | | | 128/205.24 |

| | | | | | |
|---|---|---|---|---|---|
| 2004/0154617 | A1 | * | 8/2004 | Enk | ................... A61M 16/0833 |
| | | | | | 128/203.12 |
| 2011/0264005 | A1 | * | 10/2011 | Willeford | ............... A61B 1/012 |
| | | | | | 600/156 |
| 2013/0035593 | A1 | * | 2/2013 | Lampropoulos | ...... A61M 39/10 |
| | | | | | 600/431 |

(Continued)

FOREIGN PATENT DOCUMENTS

EP          1386635  A1  *  2/2004    ........ A61M 39/0247

OTHER PUBLICATIONS

Kreider et al. (Year: 2003) "Bronchoscopy for Atelectasis in the ICU: A Case Report and Review of the Literature".*

(Continued)

*Primary Examiner* — Brandy S Lee
*Assistant Examiner* — Sara K Toich
(74) *Attorney, Agent, or Firm* — C. Brandon Browning; Maynard Nexsen PC

(57) ABSTRACT

An oxygen insufflation device can include proximal, intermediate, and distal tubes in fluid communication. The proximal end of the proximal tube can include a first tube that can be coupled to a first oxygen source and a second tube that can be coupled to a second oxygen source. The first and second tubes can be coupled to a y-coupler, which can couple to the intermediate tube at a distal end of the y-coupler. Check valves can be provided between each of the first tube and second tube and the y-coupler. The intermediate tube can include a stopcock to selectively occlude fluid communication between the proximal and distal tubes. The distal tube can include a pressure relief valve configured to relieve pressure past a predetermined threshold. A distal end of the distal tube can provide oxygen insufflation. Methods of use of the oxygen insufflation device are also provided.

17 Claims, 3 Drawing Sheets

(56)                    References Cited

U.S. PATENT DOCUMENTS

| | | | |
|---|---|---|---|
| 2015/0099993 A1* | 4/2015 | Weaver | A61M 16/0463 |
| | | | 600/531 |
| 2018/0344142 A1* | 12/2018 | Abouzgheib | A61M 5/20 |
| 2022/0233790 A1* | 7/2022 | Koltz, Jr. | A61B 17/3423 |

OTHER PUBLICATIONS

Roh et al. "Utility of oxygen insufflation through working channel during fiberoptic intubation in apneic patients: a prospective randomized controlled study" (Year: 2020).*

* cited by examiner

PATIENT INSUFFLATION SYSTEMS AND METHODS

TECHNICAL FIELD

The present invention is directed to patient insufflation system and methods, and more particularly to a medical device configured to provide insufflation to a patient and prevent over pressurization of a patient's airways and methods of use thereof.

BACKGROUND

In anesthesia, there are many procedures that require delivery of oxygen, such as during rigid bronchoscopy, direct laryngoscopy, microlaryngoscopy, one-lung ventilation cases, needle cricothyrotomy for emergency airway, but where the patient cannot be ventilated and/or intubated due to the nature of such procedures.

One of the current solutions to this problem is jet ventilation. Jet ventilation, however has a high learning curve for the operator of jet the ventilation apparatus and can be dangerous to the patient due to the high risk of pneumothorax, pneumomediastinum, and subcutaneous emphysema. The aforementioned risks also apply to other solutions, such as the rapid O2 device and the Enk modulator, because such devices supply oxygen directly from a wall flowmeter at 50 psi with no pressure regulator. In other words, jet ventilation requires a practitioner to be very proficient and usually requires a second practitioner to be present during use. The rapid O2 device and Enk oxygen flow modulator each also rely on subjective practitioner timing and assessment for adjustment of pressure and flow release as opposed to being able to rely on an objective pressure release valve coupled to such devices.

Accordingly, there is a need for patient insufflation systems and methods that can provide oxygen insufflation but can simultaneously protect patients from over pressurization of the patient's airways. The embodiments described in the present disclosure are directed to these and other considerations.

SUMMARY OF THE INVENTION

In one aspect, a medical device for providing oxygen insufflation is disclosed. The medical device can include a proximal tube, an intermediate tube, and a distal tube. The proximal tube, the intermediate tube, and the distal tube can be in fluid communication. The proximal end of the proximal tube can include a first oxygen source coupler and a second oxygen source coupler. The first oxygen source coupler can include a first tube and the second oxygen source coupler can include a second tube. The first tube and the second tube can be separate tubes. A distal end of the proximal tube can include a first check valve coupled to the first tube and a second check valve coupled to the second tube. Distal of the first check valve, the first tube can connect to a y-coupler that is approximate a proximal end of the intermediate tube. Distal of the second check valve, the second tube can connect to the y-coupler approximate the proximal end of the intermediate tube. The intermediate tube can include a stopcock configured to selectively occlude fluid communication between the proximal tube and the distal tube. A proximal end of the distal tube can include a pressure relief valve configured to relieve pressure past a predetermined pressure threshold. A distal end of the distal tube can be configured to provide oxygen insufflation to an airway of the patient.

In some embodiments, the first oxygen source coupler can include an adaptor configured for connecting the medical device to an anesthesia breathing circuit or common gas outlet. In some embodiments, the first oxygen source coupler can include a luer lock that includes a male end and a female end. The female end of the luer lock can be configured to couple to the proximal end of the proximal tube. The male end can be configured to couple to the anesthesia breathing circuit or common gas outlet.

In some embodiments, the second oxygen source coupler can include a threaded oxygen fitting configured to couple to an in-wall medical oxygen source.

In some embodiments, the proximal tube is coupled to the intermediate tube with a luer lock.

In some embodiments, the stopcock is located on a distal end of the intermediate tube.

In some embodiments, the stopcock is coupled to the proximal end of the distal tube with a luer lock.

In some embodiments, the predetermined pressure threshold is approximately 1.5 psi.

In another aspect, a medical device for providing oxygen insufflation is disclosed. The medical device can include a proximal tube including a distal end and a proximal end. The medical device can include an intermediate tube. The medical device can include a distal tube. The proximal tube, the intermediate tube, and the distal tube can be in fluid communication. The distal end of the proximal tube can include a y-coupler that is coupled to the intermediate tube. The proximal end of the proximal tube can include a y-coupler that is coupled to the intermediate tube. The proximal end of the proximal tube can include a first tube and a second tube. The first tube and the second tube can include a first oxygen source coupler and a second oxygen source coupler, respectively, at the proximal end of the proximal tube. A distal end of the first tube can include a first check valve coupled to the y-coupler. A distal end of the second tube can include a second check valve coupled to the y-coupler. The intermediate tube can include a stopcock configured to selectively occlude fluid communication between the proximal tube and the distal tube. The proximal end of the distal tube can include a pressure relief valve configured to relieve pressure past a predetermined pressure threshold. A distal end of the distal tube can be configured to provide oxygen insufflation to an airway of a patient.

In some embodiments, the first oxygen source coupler can include an adaptor configured for connecting the medical device to an anesthesia breathing circuit or common gas outlet. In some embodiments, the first oxygen source coupler can include a luer lock that includes a male end and a female end. The female end can be configured to couple to the proximal end of the proximal tube. The male end can be configured to couple to the anesthesia breathing circuit or common gas outlet.

In some embodiments, the second oxygen source coupler can include a threaded oxygen fitting configured to couple to an in-wall medical oxygen source.

In some embodiments, the stopcock is located on a distal end of the intermediate tube.

In some embodiments, predetermined pressure threshold is approximately 1.5 psi.

In some embodiments, a distal end of the y-coupler is coupled to the intermediate tube with a luer lock.

In another aspect, a method of providing oxygen insufflation for a patient is disclosed. The method can include providing an oxygen insufflation device that includes a proximal tube, an intermediate tube, and a distal tube. The proximal tube, the intermediate tube, and the distal tube can be in fluid communication. The proximal end of the proximal tube can include a first oxygen source coupler and a second oxygen source coupler. The first oxygen source coupler can include a first tube and the second oxygen source coupler can include a second tube. The first tube and the second tube can be separate tubes. A distal end of the proximal tube can include a first check valve coupled to the first tube and a second check valve coupled to the second tube. Distal of the first check valve, the first tube can connect to a y-coupler that is approximate a proximal end of the intermediate tube. Distal of the second check valve, the second tube can connect to the y-coupler approximate the proximal end of the intermediate tube. The intermediate tube can include a stopcock configured to selectively occlude fluid communication between the proximal tube and the distal tube. A proximal end of the distal tube can include a pressure relief valve configured to relieve pressure past a predetermined pressure threshold. A distal end of the distal tube can be configured to provide oxygen insufflation to an airway of the patient. The method can include connecting at least one of the first oxygen source coupler and the second oxygen source coupler to an oxygen source. The method can include inserting the distal end of the distal tube into the airway of the patient. The method can include causing the pressure relief valve to relieve at least some pressure from the oxygen insufflation device.

In some embodiments, the pressure relief valve is configured to relieve pressure above approximately 1.5 psi.

In some embodiments, connecting at least one of the first oxygen source coupler and the second oxygen source coupler to an oxygen source includes connecting the first oxygen source coupler to an anesthesia breathing circuit or common gas outlet.

In some embodiments, connecting at least one of the first oxygen source coupler and the second oxygen source coupler to an oxygen source includes connecting the second oxygen source coupler to an in-wall medical oxygen source.

In some embodiments, the method can further include terminating oxygen flow to the patient by selectively occluding fluid communication between the proximal tube and the distal tube with the stopcock.

BRIEF DESCRIPTION OF THE DRAWINGS

The present disclosure can be better understood, by way of example only, with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

The present disclosure is directed to a medical device for providing oxygen insufflation to a patient undergoing procedures that otherwise make it difficult to be ventilated and/or intubated, such as, for example but not limited to rigid bronchoscopy, direct laryngoscopy, microlaryngoscopy, one-lung ventilation cases, and needle cricothyrotomy for emergency airway.

The terms "about" and "approximately" shall generally mean an acceptable degree of error or variation for the quantity measured given the nature or precision of the measurements. Typical, exemplary degrees of error or variation are within 20 percent (%), preferably within 10%, more preferably within 5%, and still more preferably within 1% of a given value or range of values. Numerical quantities given in this description are approximate unless stated otherwise, meaning that the term "about" or "approximately" can be inferred when not expressly stated.

The terminology used herein is for the purpose of describing particular embodiments only and is not intended to be limiting. As used herein, the singular forms "a", "an", and "the" are intended to include the plural forms as well (i.e., "at least one" of what is described), unless the context clearly indicates otherwise. In every case, use of singular articles and pronouns should be interpreted to support claims to at least one of what is described, and to support claims to exactly one of what is described.

Terms such as "at least one of A and B" should be understood to mean "only A, only B, or both A and B." The same construction should be applied to longer lists (e.g., "at least one of A, B, and C").

Figure 1:
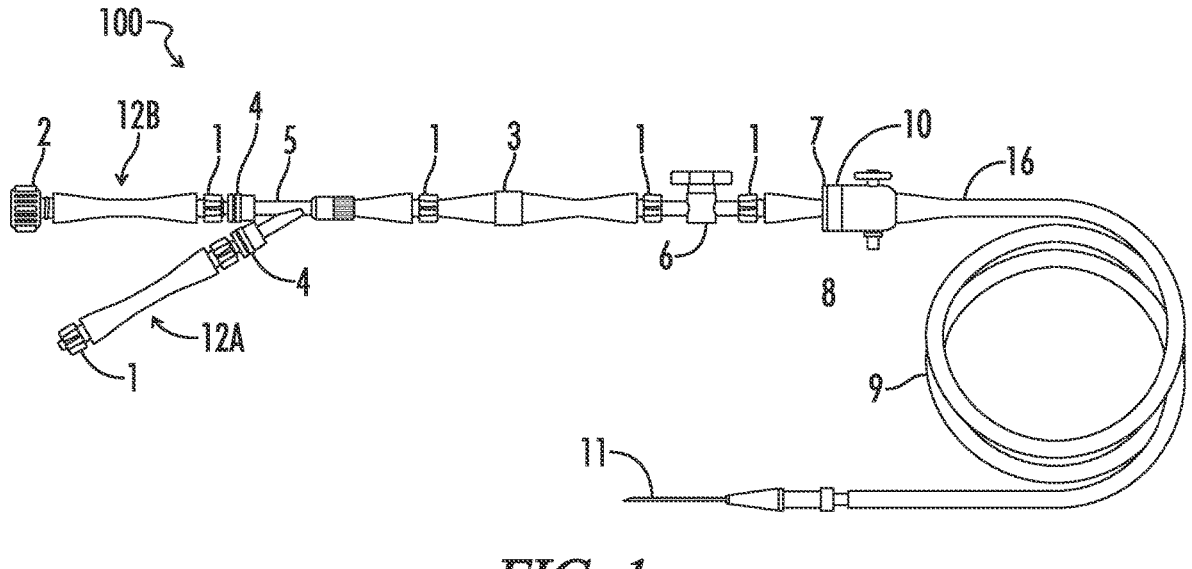
FIG. 1 depicts a medical device for providing oxygen insufflation, according to aspects of the present disclosure.

FIG. 1 depicts an oxygen insufflation device 100. As shown in FIG. 1, the medical insufflation device can include a proximal tube 12A, 12B (collectively proximal tube 12), an intermediate tube 14, and a distal tube 16. Each of the proximal tube 12, intermediate tube 14, and distal tube 16 can be constructed of medical tubing 9. Proximal tube 12, intermediate tube 14, and distal tube 16 can be in fluid communication. As shown, proximal tube 12 can have a first tube 12A and a second tube 12B. First tube 12A can include a first oxygen source coupler 1 on a proximal end of first tube 12A. Similarly, second tube 12B can include a second oxygen source coupler 2 on a proximal end of second tube 12B. First oxygen source coupler 1 can be configured to connect to an end tidal port of an anesthesia breathing circuit or common gas outlet (not pictured). In some embodiments, first oxygen source coupler can be a luer lock having a female end configured to fit into the proximal end of the first tube 12A and a male end configured to fit into the end tidal port of an anesthesia breathing circuit or common gas outlet. Second oxygen source coupler 2 can be configured to connect to a wall-based oxygen flowmeter. In some embodiments, oxygen source coupler 2 can be a threaded coupler configured to couple the second tube 12B to the wall-based oxygen flowmeter. The distal end of proximal tube 12 can be configured to couple to a y-coupler 5. That is, distal end of first tube 12A and distal end of second tube 12B each fit into a respective proximal ends of y-coupler 5. In some embodiments, check valves 4 can be disposed on each proximal end of y-coupler 5. Check valves 4 can be configured to prevent the passage of fluid (e.g., oxygen) from intermediate tube 14 towards either branch 12A, 12b of proximal tube 12. The distal end of y-coupler 5 can be configured to couple to intermediate tube 14. In some configurations, y-coupler 5 couples to intermediate tube 14 via a luer lock 1. Intermediate tube 14 can include a barbed flow-control orifice 3. Flow control orifice 3 can be configured to regulate the flow of fluid (e.g., oxygen) through oxygen insufflation device 100 such that a constant flow rate of fluid can be achieved.

Distal of the flow control orifice 3, the intermediate tube 14 can include a stopcock 6. Stopcock 6 can be coupled to the intermediate tube 14 with a pair of luer locks 1 placed on both proximal and distal ends of stopcock 6. Stopcock 6 can be configured to selectively occlude fluid communication between proximal tube 12 and distal tube 16. Stopcock 6 can allow an operator of oxygen insufflation device 100 to quickly terminate the flow of oxygen through the oxygen insufflation device 100 no matter the oxygen source being used. For example, the stopcock 6 can terminate flow of oxygen if used with either end tidal port of anesthesia breathing circuit/common gas outlet or wall-based oxygen flowmeter.

Distal end of intermediate tube 14 can be coupled to distal tube 16 via a pressure relief valve adaptor 7. Distal of pressure relief valve adaptor 7 can be disposed a pressure relief valve 8. In some embodiments, pressure relief valve 8 can be permanently coupled to relief valve adaptor 7 with medical epoxy 10. Distal of pressure relief valve adaptor 8, distal tube 16 can continue with a length of medical tubing 9. The distal end of distal tube 16 can terminate in insufflation end 11. Insufflation end 11 can be varied for whatever device is appropriate for the specific operation (e.g., catheter, laryngoscope, bronchoscope, etc.). For illustrative purposes only, insufflation end 11 is shown as a catheter, but this illustration is intended to be non-limiting.

According to some embodiments, pressure relief valve 8 can be configured to release excess pressure past a predetermined pressure threshold. In some embodiments, the predetermined pressure threshold can be approximately 1.5 psi. That is, once the pressure exceeds 1.5 psi within oxygen insufflation device 100, the pressure relief valve 8 can open, thereby preventing the patient from experiencing dangerous insufflation pressure without further intervention by the operator of oxygen insufflation device 100.

According to some embodiments, either first oxygen source coupler 1 or second oxygen source coupler 2 can be utilized to provide oxygen through oxygen insufflation device 100. Although oxygen insufflation device 100 has been described with respect to providing oxygen to a patient, any medically appropriate gas mixture may be utilized (e.g., nitrous oxide, oxygen, etc.). Check valves 4 can prevent fluid from traveling between first tube 12A and second tube 12B and vice versa. That is, if first tube 12A is coupled to an oxygen source, the oxygen may be prevented from flowing into second tube 12B. Rather, oxygen can flow from first tube 12A, through intermediate tube 14, through distal tube 16, and through insufflation end 11 to the patient. Similarly, if second tube 12B is coupled to an oxygen source, the oxygen may be prevented from flowing into the first tube 12A. Rather, oxygen can flow from second tube 12B, through intermediate tube 14, through distal tube 16, and through insufflation end 11 to the patient. In some embodiments, the locations of flow orifice 3, stopcock 6, and pressure release valve 8 can be interchangeable within oxygen insufflation device 100.

In some embodiments, both first oxygen source coupler 1 and second oxygen source coupler 2 can simultaneously be coupled to first and second oxygen sources, respectively. Check valves 4 can keep pressure from either oxygen source from being fed backwards towards the other oxygen source. Pressure relief valve 8 can ensures that the pressure within the oxygen insufflation device 100 does not exceed the predetermined pressure threshold, keeping the patient safe from over pressurization.

Figure 2:
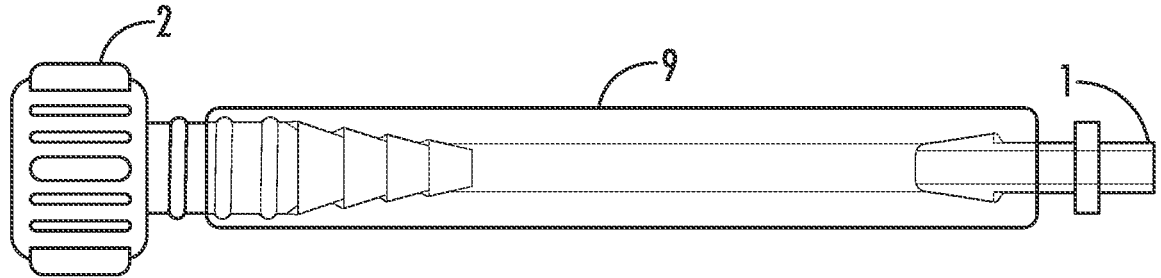
FIG. 2 depicts an oxygen source coupler, according to aspects of the present disclosure.

FIG. 2 shows second oxygen source coupler 2, as previously described with respect to FIG. 1. As shown, oxygen source coupler 2 can be a threaded oxygen fitting. The threaded oxygen fitting can be configured to couple to an in-wall medical oxygen source. On a distal end of threaded oxygen fitting can be a barbed tip that is configured to compression fit into medical tubing 9 of second tube 12B. Luer lock 1 can be disposed on distal end of second tube 12B and be configured to couple second tube 12B to y-coupler 5, as previously described with respect to FIG. 1.

Figure 3:
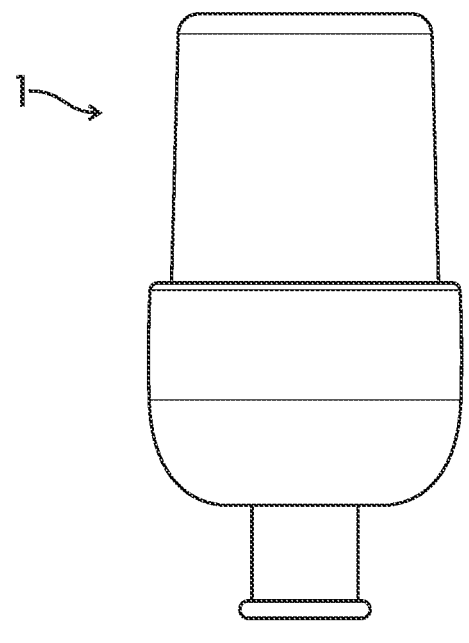
FIG. 3 depicts another oxygen source coupler, according to aspects of the present disclosure.

FIG. 3 shows a first oxygen coupler 1 as a luer lock having a female end and a male end. The female end, as shown at the bottom end of FIG. 3 of luer lock 1 can be configured to couple to the proximal end of first tube 12A. The male end, as shown at the top end of FIG. 3 can be configured to couple the first tube 12A to an end tidal port of an anesthesia breathing circuit or common gas outlet.

Figure 4:
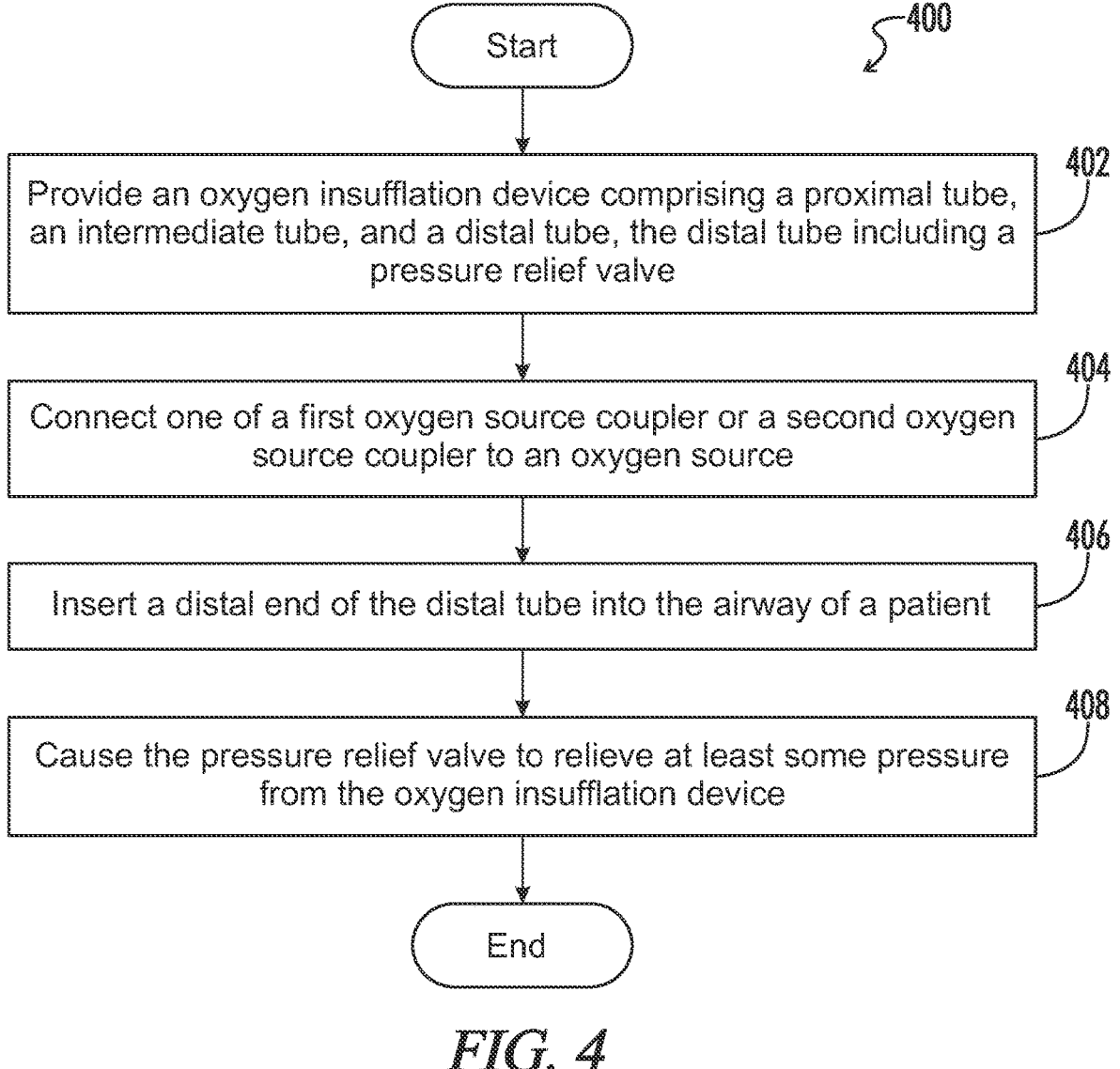
FIG. 4 is a flowchart demonstrating an exemplary method of providing oxygen insufflation to a patient, according to aspects of the present disclosure.

FIG. 4 is a flowchart demonstrating an exemplary method 400 of using the oxygen insufflation device 100. In step 402, the method can include providing an oxygen insufflation device 100. The oxygen insufflation device 100 can be provided as described with respect to FIG. 1. In some embodiments, the oxygen insufflation device 100 can include a proximal tube 12 including a distal end and a proximal end, an intermediate tube 14, and a distal tube 16. The proximal tube 12, the intermediate tube 14, and the distal tube 16 can be in fluid communication. The distal end of the proximal tube 12 can include a y-coupler 5 that is coupled to the intermediate tube 14. The proximal end of the proximal tube 12 can include a first tube 12A and a second tube 12B. The first tube 12A and the second tube 12B can include a first oxygen source coupler 1 and a second oxygen source coupler 2, respectively, at the proximal end of the proximal tube 12. A distal end of the first tube 12A can include a first check valve 4 that is coupled to the y-coupler 5. A distal end of the second tube 12B can include a second check valve 4 that is coupled to the y-coupler 5. The intermediate tube 14 can include a stopcock 6 that is configured to selectively occlude fluid communication between the proximal tube 12 and the distal tube 16. A proximal end of the distal tube 16 can include a pressure relief valve 8 that is configured to relieve pressure past a predetermined pressure threshold. A distal end (e.g. insufflation end 11) of the distal tube 16 is configured to provide oxygen insufflation to an airway of a patient.

In step 404, the method can include connecting at least one of first oxygen source coupler 1 and the second oxygen source coupler 2 to an oxygen source. As described with respect to FIG. 1, at least one of the first oxygen source coupler 1 or second oxygen source coupler 2 can be connected to an oxygen source. The oxygen source can be the end tidal port of an anesthesia breathing circuit/common gas outlet and/or an in-wall medical oxygen source. In some embodiments, both first oxygen source coupler 1 and second oxygen source coupler 2 can be simultaneously coupled to oxygen sources.

In step 406, the method can include inserting a distal end (e.g., insufflation end 11) of distal tube 14 into the airway of a patient. In step 408, the method can include causing the pressure relief valve 8 to relieve at least some pressure form the oxygen insufflation device 100.

In some embodiments, the pressure relief valve is configured to relieve pressure above approximately 1.5 psi.

In some embodiments, connecting one of the first oxygen source coupler 1 or the second oxygen source coupler 2 to an oxygen source includes connecting the first oxygen source coupler 1 to an anesthesia breathing circuit or common gas outlet, for example to the end tidal port of the anesthesia breathing circuit or common gas outlet.

In some embodiments, connecting one of the first oxygen source coupler 1 or the second oxygen source coupler 2 to an oxygen source includes connecting the second oxygen source coupler 2 to an in-wall medical oxygen source.

In some embodiments, the method can include terminating oxygen flow to the patient by selectively occluding fluid communication between the proximal tube 12 and the distal tube 16 with the stopcock 6.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

As a further example, variations of apparatus or process parameters (e.g., dimensions, configurations, components, process step order, etc.) may be made to further optimize the provided structures, devices, and methods, as shown and described herein. In any event, the structures and devices, as well as the associated methods, described herein have many applications. Therefore, the disclosed subject matter should not be limited to any single embodiment described herein, but rather should be construed in breadth and scope in accordance with the appended claims.

What is claimed is:

1. A medical device for providing oxygen insufflation comprising:
   a proximal tube;
   an intermediate tube; and
   a distal tube;
   wherein:
      the proximal tube, the intermediate tube, and the distal tube are in fluid communication;
      a proximal end of the proximal tube comprises a first oxygen source coupler and a second oxygen source coupler, the first oxygen source coupler comprising a first tube and the second oxygen source coupler comprising a second tube, wherein the first tube and the second tube comprise separate tubes;
      a distal end of the proximal tube comprises a first check valve coupled to the first tube and a second check valve coupled to the second tube;
      a distal end of the first check valve of the first tube connects to a y-coupler approximate a proximal end of the intermediate tube;
      a distal end of the second check valve of the second tube connects to the y-coupler approximate the proximal end of the intermediate tube;
      the intermediate tube comprises a stopcock configured to selectively occlude fluid communication between the proximal tube and the distal tube;
      a proximal end of the distal tube comprises a pressure relief valve configured to relieve pressure past a predetermined pressure threshold of approximately 1.5 psi; and
      a distal end of the distal tube is configured to provide oxygen insufflation to an airway of a patient.

2. The system of claim 1, wherein the first oxygen source coupler comprises an adaptor configured for connecting the medical device to an anesthesia breathing circuit or common gas outlet.

3. The system of claim 2, wherein the first oxygen source coupler comprises a luer lock comprising a male end and a female end, the female end configured to couple to the proximal end of the proximal tube and the male end configured to couple to the anesthesia breathing circuit or common gas outlet.

4. The system of claim 1, wherein the second oxygen source coupler comprises a threaded oxygen fitting configured to couple to an in-wall medical oxygen source.

5. The system of claim 1, wherein the proximal tube is coupled to the intermediate tube with a luer lock.

6. The system of claim 1, wherein the stopcock is located on a distal end of the intermediate tube.

7. The system of claim 6, wherein the stopcock is coupled to the proximal end of the distal tube with a luer lock.

8. A medical device for providing oxygen insufflation comprising:
   a proximal tube comprising a distal end and a proximal end;
   an intermediate tube; and
   a distal tube;
   wherein:
      the proximal tube, the intermediate tube, and the distal tube are in fluid communication;
      the distal end of the proximal tube comprises a y-coupler that is coupled to the intermediate tube;
      the proximal end of the proximal tube comprises a first tube and a second tube, wherein the first tube and the second tube comprise a first oxygen source coupler and a second oxygen source coupler, respectively, at the proximal end of the proximal tube;
      a distal end of the first tube comprises a first check valve coupled to the y-coupler;
      a distal end of the second tube comprises a second check valve coupled to the y-coupler;
      the intermediate tube comprises a stopcock configured to selectively occlude fluid communication between the proximal tube and the distal tube;
      a proximal end of the distal tube comprises a pressure relief valve configured to relieve pressure past a predetermined pressure threshold of approximately 1.5 psi; and
      a distal end of the distal tube is configured to provide oxygen insufflation to an airway of a patient.

9. The system of claim 8, wherein the first oxygen source coupler comprises an adaptor configured for connecting the medical device to an anesthesia breathing circuit or common gas outlet.

10. The system of claim 9, wherein the first oxygen source coupler comprises a luer lock comprising a male end and a female end, the female end configured to couple to the proximal end of the proximal tube and the male end configured to couple to the anesthesia breathing circuit or common gas outlet.

11. The system of claim 8, wherein the second oxygen source coupler comprises a threaded oxygen fitting configured to couple to an in-wall medical oxygen source.

12. The system of claim 8, wherein the stopcock is located on a distal end of the intermediate tube.

13. The system of claim 8, wherein a distal end of they-coupler is coupled to the intermediate tube with a luer lock.

14. A method of providing oxygen insufflation for a patient, comprising:
   providing an oxygen insufflation device comprising a proximal tube, an intermediate tube, and a distal tube, wherein:

the proximal tube, the intermediate tube, and the distal tube are in fluid communication;

a proximal end of the proximal tube comprises a first oxygen source coupler and a second oxygen source coupler, the first oxygen source coupler comprising a first tube and the second oxygen source coupler comprising a second tube, wherein the first tube and the second tube comprise separate tubes;

a distal end of the proximal tube comprises a first check valve coupled to the first tube and a second check valve coupled to the second tube;

a distal end of the first check valve of the first tube connects to a y-coupler approximate a proximal end of the intermediate tube;

a distal end of the second check valve of the second tube connects to the y-coupler approximate the proximal end of the intermediate tube;

the intermediate tube comprises a stopcock configured to selectively occlude fluid communication between the proximal tube and the distal tube;

a proximal end of the distal tube comprises a pressure relief valve configured to relieve pressure past a predetermined pressure threshold of approximately 1.5 psi; and a distal end of the distal tube is configured to provide oxygen insufflation to an airway of a patient;

connecting at least one of the first oxygen source coupler and the second oxygen source coupler to an oxygen source;

inserting the distal end of the distal tube into the airway of the patient; and causing the pressure relief valve to relieve at least some pressure from the oxygen insufflation device.

15. The method of claim 14, wherein connecting at least one of the first oxygen source coupler and the second oxygen source coupler to an oxygen source comprises connecting the first oxygen source coupler to an anesthesia breathing circuit or common gas outlet.

16. The method of claim 14, wherein connecting at least one of the first oxygen source coupler and the second oxygen source coupler to an oxygen source comprises connecting the second oxygen source coupler to an in-wall medical oxygen source.

17. The method of claim 14, further comprising terminating oxygen flow to the patient by selectively occluding fluid communication between the proximal tube and the distal tube with the stopcock.

* * * * *